United States Patent [19]

Foley et al.

[11] Patent Number: 5,645,049
[45] Date of Patent: Jul. 8, 1997

[54] EXHALATION VALVE FOR FACE MASK WITH SPACER CHAMBER CONNECTION

[75] Inventors: Martin P. Foley; Robert Morton, both of London, Canada

[73] Assignee: Trudell Medical Limited, London, Canada

[21] Appl. No.: 270,752

[22] Filed: Jul. 5, 1994

Related U.S. Application Data

[63] Continuation-in-part of Ser. No. 973,280, Nov. 9, 1992, abandoned.

[51] Int. Cl.[6] .......................... A61M 16/00; A62B 18/02; A62B 18/10
[52] U.S. Cl. ........................ 128/203.29; 128/206.28; 128/207.12; 128/200.23
[58] Field of Search .................. 128/200.14, 200.23, 128/203.12, 203.29, 205.25, 206.21, 207.12, 200.29, 205.23, 206.28

[56] References Cited

U.S. PATENT DOCUMENTS

| | | |
|---|---|---|
| 374,831 | 12/1887 | Harrington . |
| 440,713 | 11/1890 | Krohne et al. ............... 128/205.23 |
| 1,695,170 | 12/1928 | Burdick . |
| 1,998,327 | 4/1935 | McGuire . |
| 2,164,330 | 7/1939 | Katz et al. . |
| 2,381,568 | 8/1945 | Booharin . |
| 2,432,946 | 12/1947 | Theunissen . |
| 2,848,994 | 8/1958 | Aguado . |
| 2,931,356 | 4/1960 | Schwarz . |
| 2,985,169 | 5/1961 | Elling ............................... 128/42 |
| 3,232,292 | 2/1966 | Schaefer ......................... 128/172 |
| 3,490,452 | 1/1970 | Greenfield . |
| 4,809,692 | 3/1989 | Nowacki et al. . |
| 4,832,015 | 5/1989 | Nowacki et al. . |
| 4,865,027 | 9/1989 | Laanen et al. . |
| 5,012,803 | 5/1991 | Foley et al. .................. 128/200.23 |
| 5,109,839 | 5/1992 | Blasdell et al. .............. 128/203.12 |

Primary Examiner—Kimberly L. Asher
Attorney, Agent, or Firm—Brinks Hofer Gilson & Lione

[57] ABSTRACT

A mask is provided for the inhalation of medication, such as asthmatic medication. The mask is molded of a resilient plastic or rubber material and has a central through opening and includes an open front portion adapted to receive an aerosolization chamber which receives medication from a metered dose inhaler. A sidewall expands outwardly from the open front portion and is adapted to fit sealingly on a face covering the mouth and nose. The sidewall is provided with an extension to accommodate the nose. A one-way exhalation valve is provided in the mask, preferably at the far end of the nose accommodating extension for conveying exhaled air to the outside, and preventing entrance of outside air therethrough into said mask.

27 Claims, 2 Drawing Sheets

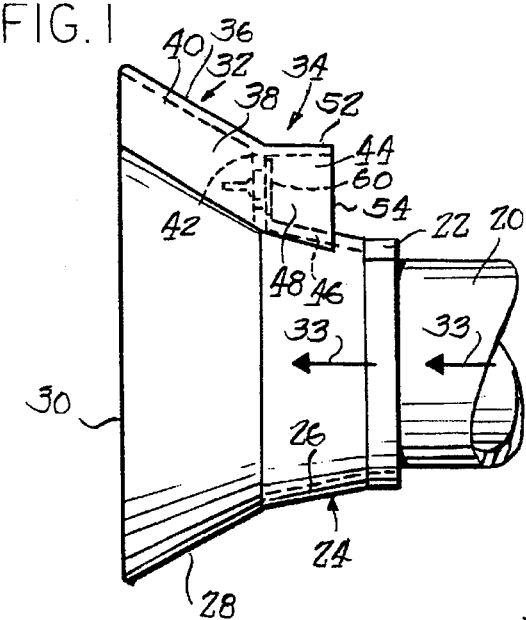

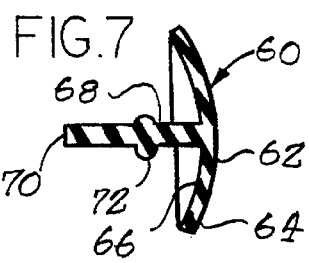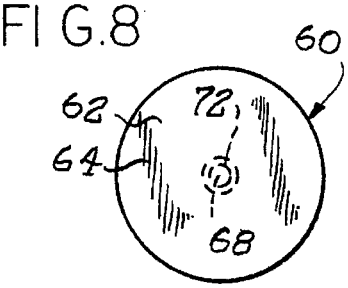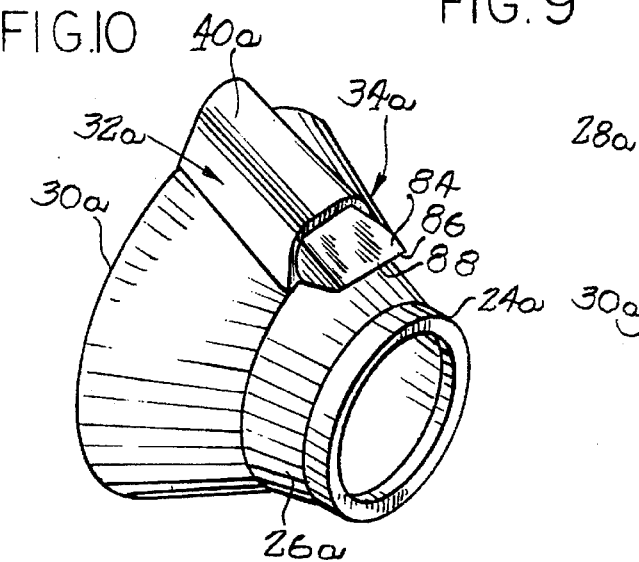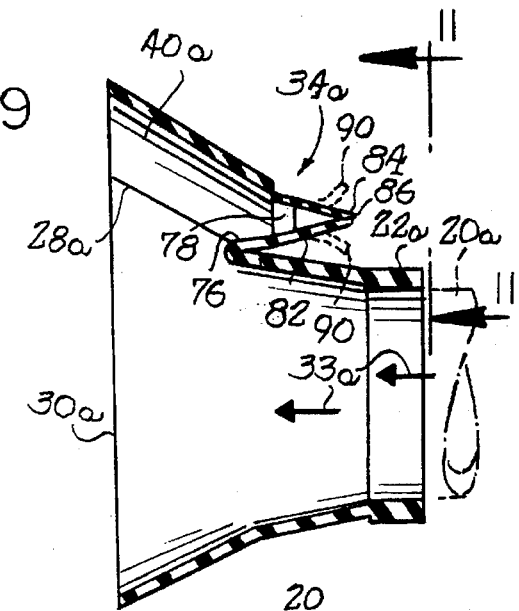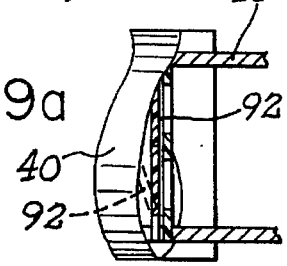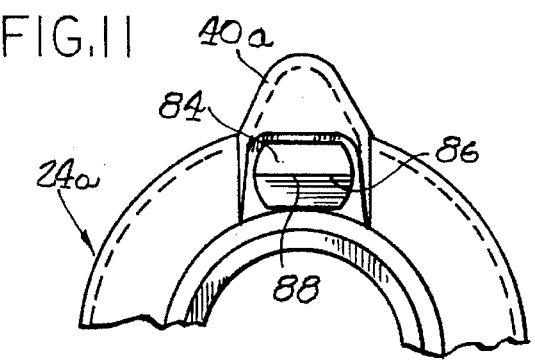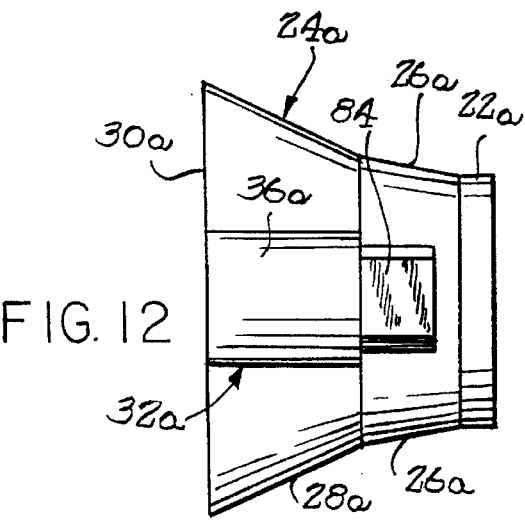

EXHALATION VALVE FOR FACE MASK WITH SPACER CHAMBER CONNECTION

REFERENCE TO RELATED APPLICATION

This application is a continuation-in-part of Ser. No. 07/973,280, filed Nov. 9, 1992, now abandoned.

BACKGROUND OF THE INVENTION

Breathing problems due to allergies, asthma, etc. are widespread. It is known that such problems can be helped with inhalation of appropriate medication, such as a beta agonist. Small cartridges containing such medication are provided. Each cartridge has a valve which when activated dispenses a predetermined quantity of medication as a spray. Such devices are known as metered dose inhalers (MDI). Such metered dose inhalers are rather inefficient in delivering the medication to the patient. It is known that provision of some sort of an inhalation chamber between the MDI and the patient's mouth materially improves delivery to the patient. One such device that has met rather considerable commercial success is disclosed and claimed in Nowacki et al U.S. Pat. No. 4,470,412.

Further problems are encountered with delivery of anti-asthmatic medication to children. With adults in otherwise reasonably good health the patient generally can be relied upon to handle the matter himself, or to communicate with a healthcare provider. However, children, particularly infants, cannot readily follow directions, and often cannot communicate with a healthcare provider. Accordingly, efforts have been made so that a healthcare provider can readily observe whether a small child or infant is properly inhaling and exhaling, and thereby taking in the necessary medication. Two inhalers for this purpose are shown in Nowacki et al U.S. Pat. No. 4,809,692, and in Nowacki et al U.S. Pat. No. 4,832,015. It has been found in practice that anxious mothers often produce false readings with infants and other small children, and it further has been found that producing requisite plastic moldings at a commercially acceptable cost has been difficult.

In the last two U.S. patents noted above a small mask is attached to the exit end of the aerosolizing chamber to engage an infant's face to ensure proper movement of the vaporized or aerosolized medication from the chamber into the patient's mouth and nose. Such mask is generally made of a plastic or rubber material. In the first of these two patents a whistle is provided that operates upon inhalation or exhalation of the patient (or both) so that a sound will be produced that can be observed by a healthcare provider. However, the sound is not very loud, and is sometimes indiscernable in conditions of relatively high ambient noise levels. In the second of such two patents a bubble of thinner material is formed integral with the mask, and is intended to move in and out with inhalation and exhalation. The bubble must be thin enough to flex readily, but not so thin as to tear or otherwise fracture. Molding of the mask to produce a relatively thick mask, and the extremely thin integral bubble is difficult.

It will be recognized that a person who is elderly, or who is sick, or who is in some manner incapacitated may present many of the same problems of communicating with or being observed by a healthcare provider as with infants.

OBJECTS OF THE PRESENT INVENTION

In accordance with the principles of the present invention it is an object thereof to provide a mask for inhalation of medication, such as asthmatic medication, which has an exhalation valve that is closed upon rest or upon inhalation, but which discernably moves to an open position upon exhalation by the patient.

It is a further object of the present invention to provide an exhalation valve in a medication mask which is closed at rest or on inhalation, and which is readily observable as being closed, and which positively opens in a readily discernable manner upon exhalation, which valve is simple and positive, and readily produced at low cost.

In carrying out the principles of the present invention a pediatric mask is provided such as in U.S. Pat. Nos. 4,809,692 and 4,832,015 mentioned above. The preferred material for molding such mask is silicone rubber. This material can be autoclaved for sterilization, and is well accepted by the medical profession and governmental bodies that might have to approve of the mask. The mask is translucent, and hence it is possible to see at least a limited distance therethrough. In a preferred form of the invention a valve member is also molded of silicone rubber and is assembled with the balance of the mask by means of an insert and pull operation, with no added fastener being required. In a second form of the invention the valve is molded as an integral part of the mask. Other types of observable one-way air valves are contemplated but the two herein are sufficient for illustration.

THE DRAWINGS

The invention will best be understood with reference to the following specification when taken in connection with the accompanying drawings wherein:

FIG. 1 is a side view of a preferred form of mask having an exhalation valve therein;

FIG. 2 is a view taken from the right side of FIG. 1, comprising an end view of the mask;

FIG. 3 is a view similar to FIG. 2 but before installation of the valve;

FIG. 4 is a sectional view of the valve and a portion of the mask on an enlarged scale as taken along the line 4—4 in FIG. 3;

FIG. 5 is an end view of the valve and adjacent portion of the mask as taken from the right end of FIG. 4 on a further enlarged scale;

FIG. 6 is a perspective view of the mask;

FIG. 7 is a side view on an enlarged scale of the closure member of the valve;

FIG. 8 is a view of the valve closure member as taken from the right side of FIG. 7;

FIG. 9 is an axial sectional view of a second embodiment of the mask;

FIG. 9a is a figure similar to FIG. 9, and representing an additional part;

FIG. 10 is a perspective view of the mask of FIG. 9 as taken from above and the front end:

FIG. 11 is a fragmentary right end view of the valve portion of the mask of FIG. 9 as taken substantially along the line 11—11 in FIG. 9; and FIG. 12 is a top view of the mask of FIG. 9.

DETAILED DESCRIPTION OF THE ILLUSTRATED EMBODIMENTS

Turning now to the drawings in greater particularity, and first to FIGS. 1–8, there will be seen a cylindrical aerosolization chamber 20 (FIG. 1). This chamber is only shown in part, since it may be the same as that shown in Nowacki et al U.S. Pat. No. 4,470,412 or in Foley et al U.S. Pat. No. 5,012,803, except that the exhalation ports in the aerosolization chamber are deleted. The aerosolization chamber is molded of a semi-rigid plastic, and the exit end thereof is inserted within a gripping ring 22 at the upstream end of a mask 24 molded of suitable material which is sufficiently pliable to conform to an infant's face. A preferred material is translucent silicone rubber. The mask includes a first frustoconical portion 26 of rather shallow taper integral with the ring 22, and a second or downstream portion 28 of frustoconical shape of greater taper. The outer edge 30 (the left edge in FIG. 1) is open, and air and medication flow through the chamber 20 and into the mask as indicated by the arrows 33. The inner surface of the ring 22 is cylindrical and is of small enough diameter to grip the rear end of the aerosolization chamber 20. The mask is circular in outline or cross section, with the exception of a nosepiece 32 and a valve 34, both of which are formed integral with the mask save for an operating or closure member in the valve to be noted hereinafter. The nosepiece 32 extends substantially from end to end of the rearward or portion of greater taper 28, with the frustoconical portion 28 opening radially into the nosepiece. The nosepiece has an outer edge 36 substantially parallel to the corresponding outer surface of the frustoconical portion 28 adjacent to the nosepiece. The nosepiece is substantially an inverted V having legs 38 joined together by an arcuate portion 40 which includes the outer edge 36. At the forward or upstream end the lowest portion of nosepiece 32 is terminated by a vertical wall 42. (The use of "upstream" is intended to refer relative to the air and medication movement through the aerosolization chamber 20 and into the mask 24, as indicated by the arrows 33.)

Forwardly or upstream of the wall 42 there is a boxlike housing 44 extending outwardly from the mask body and closed off therefrom by a portion of the first frustoconical portion 26 and forming a floor 46 to the valve body or housing. Walls 48 extend substantially vertically outwardly from the frustoconical portion 26, and taper inwardly at 50 to a flat roof 52. The upstream end of the valve body 44 is open at 54, and the downstream end of the housing is integrally sealed to the wall 42.

The wall 42 is provided with a small central opening 56 and with a pair of arcuate openings 58 concentric with and spaced horizontally from the smaller central opening 56.

A valve closure member 60 is seen best in FIGS. 7 and 8, and includes a circular head 62. The head is molded so as to be convex on the outer surface 64, and concave on the undersurface 66. Inwardly or rearwardly from the convex inner surface 66 a stem 68 extends rearwardly along the axis of the head 62. The stem somewhat closer to the undersurface 66 than to the outer end 70 of the stem is provided with an integral annular ring or enlargement 72 having a semicircular cross section.

The diameter of the stem 68 is exactly the same as the diameter of the central hole 56, and the distance from the undersurface 66 of the head 62 to the confronting edge of the enlargement 72 is the same as, or very slightly less than the thickness of the wall 42. Accordingly, to assemble the valve head 60 with the mask the end of the stem 70 is pushed through the hole 56 from the upstream surface of the wall 42. Since the enlargement 72 is spaced closer to the undersurface 66 of the valve head than it is to the outer end 70 of the stem, the outer end 70 projects through the wall 42 by the time the enlargement 72 engages the front surface of the wall. The stem adjacent the outer end 70 thus can be grasped and pulled through the hole 56. Stretching of the stem 68 somewhat reduces its diameter. The enlargement 72 is squashed inwardly by the hole 56, while the hole 56 is somewhat enlarged on a temporary basis by the enlargement 72. Thus, the enlargment 72 moves through the wall to abut the rear surface thereof as shown in FIG. 4 to hold the valve member 60 in place. The undersurface 66 of the valve head 62 is flattened against the flat front surface of the wall 42 as shown in FIG. 4. Accordingly, no air can pass through the valve structure from the upstream end (the right end in FIG. 4, for example) into the mask. However, when the infant exhales the pressure within the mask is increased. This increased pressure cannot cause backflow into the aerosolization chamber 20 due to the provision of a one-way valve 92. As shown in FIG. 9A, near the exit end (downstream end) of the aerosolization chamber. However, the air pressure passes air through the arcuate openings 58, flexing the head 62 away from the arcuate openings 58 as shown in broken lines in FIG. 4, thereby permitting exhalation by the infant. Subsequent rest or inhalation by the infant returns the interior of the mask to ambient air pressure or below, and the valve head 62 again flattens against the wall 42.

Flexure of the valve head 62 over the openings 58 is somewhat as if there were two doors pivoted about one or more vertical axes passing through or adjacent to the smaller hole 56. Such movement readily can be seen by a healthcare provider (or the infant's mother) looking into the valve body through the open end 54, or looking through the translucent walls 48, 52 of the valve body. Thus, observation of exhalation is positively assured, and there cannot be exhalation unless there is first inhalation. Thus, it is readily ascertained that the infant is breathing and inhaling the desired medication. All of the parts are large enough to resist rupture or tearing without difficulty, and are readily molded. Installation of the valve member is quick and simple, and adds very little to the overall cost of the mask. No particular close tolerances must be held to provide an integral part of the mask that must flex as has been done in at least some of the prior art.

A modification of the invention is shown in FIGS. 9–12. Many of the parts are similar to those heretofore shown and described, and are identified by the use of similar numerals with the addition of the suffix a to avoid repetition of disclosure. The mask **24*a*** is in most respects substantially the same as that disclosed and claimed in the aforesaid U.S. Pat. No. 4,832,015, but omits the flexible bubble previously used as an indicator of breathing by an infant.

An exhalation valve **34*a* is molded integrally with the remainder of the mask. It opens at its rear into the nosepiece 40*a*, and is of the type known as a duckbill valve. It includes a forwardly extending generally cylindrical section 76 tapering inwardly at a thinning frustoconical section 78 to a reduced diameter cylindrical section 80. The duckbill valve 34*a* then steps inwardly at 82 to a thinned forwardly projecting bill 84 terminating at a flat nose 86 having a slit 88 (FIG. 11) extending horizontally across it. The slit 88 is normally closed as shown by the solid line in FIG. 11. Upon inhalation pressure within the mask is reduced below ambient pressure, and the thinned side portions 84 adjacent the flat nose 86 tend to come together further to close the valve to prevent ingress of air. However, upon exhalation the slit 88 bows outwardly as shown by the broken lines 90 in FIGS. 9 and 11, whereby air readily exits from the exhalation valve 34*a***.

Both forms of the invention as herein shown and described positively prevent ingress of air through the exhalation valve, and afford egress thereof at very little pressure above ambient pressure, less than 0.50 inch of water. Since the second form of the invention in FIGS. 9–12 has the entire valve formed as an integral part of the mask no assembly step is required in producing the mask. However, molding is somewhat more difficult. In the first and preferred form of the mask as shown in FIGS. 1–8 the assembly step is extremely simple, and does not require much additional labor. Molding is greatly simplified. As has been noted earlier the enlargement 72 on the valve stem 68 avoids the necessity of any separate fastener to hold the umbrella-like valve in installed position, yet is easily moved to installed position. The valve in the first embodiment also opens readily on exhalation with less than 0.50 inch of water internal pressure above ambient, and provides positive closure against entrance of air upon inhalation. It will be appreciated that it is not desired to have air enter upon inhalation as it would dilute the medication being brought in from the aerosolization chamber 20. Exit of air through the two openings or ports 58 provides for passage of a generous amount of exhaled air.

The mask and valve are intended primarily for use with an infant or young child, and in both instances the opening of the valve is readily seen by a healthcare provider, either professional or a patent.

The mask is in primarily for use with infants and small or young children. Approximate dimensions for the mask are just over 3 inches diameter across the rear, open end 30 and just over two inches from this rear open end 30 to the front of the ring 22 gripping the aerosolization chamber. The inside diameter of the ring 22a is approximately 1.4 inches, while the wall thickness is on the order of 0.08 inch. The diameter of the valve head 62 is 0.440 inch and the thickness is 0.015 inch. The length of the valve stem 68 is 0.280 inch from the underside of the head to the end 70. The radius of the valve stem is 0.040 inch, except at the enlargement 72 where the outside diameter is 0.070. The radius of the enlargement (in axial section of the stem) is 0.015 inch.

As noted earlier, the valve opens with a very slight air pressure. An inhalation pressure of 0.5 inch of water below ambient pressure is by design and by test is sufficient to open the valve. Furthermore, the valve is recessed sufficiently as to avoid damage by searching fingers. Damage to the valve that would inhibit operation is thereby positively avoided. The valve is recessed by at least the diameter of the valve.

The mask fits very closely to the face, and the nosepiece adds little volume. Thus the total volume of the mask is not very great. Accordingly, the medication in the mask, including the nosepiece, is a minimum. The amount of air exhaled is not very great, and previously inhaled air with medication stays for inhalation by the patient. This is an important feature of the present invention. Air held in the mask by the inhalation valve (provided by the valve in the aerosolization chamber), and by the exhalation valve in the mask is retained for a second inhalation. No medication is wasted. With each breath the medication laden air is refreshed for further inhalation by the patient, and is reinforced with the addition of fresh medication laden air.

With every breath, fresh air laden with medication enters the mask from the aerosolization chamber. This air enters the mask adjacent the mouth and nose. There is very little dead space within the mask. Thus substantially all of the medication laden air is available for inhalation. The medication laden air retained within the mask by the inlet and outlet valves is available for further inhalation. The amount expelled from the mask by exhalation is just equal to fresh air with medication drawn into the air by inhalation, so that the medication is held close to the patient's face for subsequent inhalation. Very little is wasted.

As noted earlier there are some adult patients who must inhale medication, but are for one reason or another incapable of handling an aerosolization chamber and MDI personally. A similar mask of slightly larger size would be in order for such patients, with a healthcare provider or friend to observe the opening of the valve upon exhalation, and closure upon inhalation.

Particularly in the preferred form of the invention the exhalation valve is located directly adjacent the nostrils, and thereby forms a short path for exhalation from the mask.

The specific embodiments of the invention as herein shown and described are for illustrative purposes only. Various changes in structure will no doubt occur to those skilled in the art, and will be understood as forming a part of the present invention insofar us they fall within the spirit and scope of the appended claims.

The invention is claimed as follows:

1. A mask for the inhalation of medication by a human being, said mask being molded of plastic material or the like having an interior and a central through opening comprising an open front portion adapted to receive a hollow body having air with medication dispersed therein, said mask comprising:

means for minimizing dead space inside said mask yet providing efficient inhalation and exhalation flow paths that purge said mask of exhaled air;

a sidewall expanding outwardly from said front portion to a rear portion adapted to fit sealingly on a human face and covering the mouth and nose, said sidewall including a tunnel-like extension projecting outwardly of said sidewall and substantially parallel thereto, and adapted to overlie a nose, said extension extending substantially from said rear portion toward said front portion and having a front end terminating short of said front portion of said mask, and means for providing a short exhalation flow path comprising a normally closed one-way exhalation valve adjacent said front end of said extension and adapted for positioning directly adjacent the nostrils of the nose, said exhalation valve communicating on one side inwardly of said mask into said extension and on the other side communicating outwardly of said mask to outside air, said exhalation valve opening on exhalation to pass exhaled air from said mask and closing in the absence of exhaled air to prevent entry of outside air.

2. A mask as set forth in claim 1 wherein said valve is positioned in its entirety short of said front portion of said mask.

3. A mask as set forth in claim 1 and further including a transverse wall adjacent the end of said nose receiving extension relatively toward the mask open front portion, said valve being located in an opening through said transverse wall.

4. A mask as set forth in claim 3 wherein said valve includes an exhalation opening through said transverse wall and an adjacent anchor opening through said transverse wall, said valve including a valve closure element comprising a head and an integral stem of plastic material, said head normally covering said exhalation opening relatively toward the exterior of said mask and said stem extending into said anchor opening to anchor said head, said head resiliently moving at least in part from said exhalation opening upon exhalation.

5. A mask as set forth in claim 4 wherein said stem extends entirely through said transverse wall and has an enlargement thereon engaging said transverse wall opposite to said valve member head.

6. A mask as set forth in claim 5 wherein said head is resilient and flexes away from said exhalation opening upon exhalation.

7. A mask as set forth in claim 6 wherein there are two exhalation openings through said transverse wall and lying on opposite sides of said anchor opening, said head having an undersurface inherently concave and pulled substantially flat by said stem, said head flexing outwardly upon exhalation.

8. A mask as set forth in claim 1 wherein said exhalation valve comprises a duckbill valve extending from said front end of said extension toward said front end portion of said mask but terminating short of said front end portion.

9. A mask for inhalation of medication by a human being, said mask being molded of plastic material or the like having an interior and a through opening comprising a front portion adapted to receive a hollow body having air with medication dispersed therein, said mask comprising:

means for minimizing dead space inside said mask yet providing efficient inhalation and exhalation flow paths that purge said mask of exhaled air a sidewall expanding outwardly from said front portion to a rear portion adapted to fit sealingly on a human face and covering the mouth and nose, and means for providing a short exhalation flow path comprising a normally closed one-way exhalation valve in the front portion of said mask, adapted for positioning directly adjacent the nostrils of the nose, said exhalation valve including a passageway through said front portion and having a transverse wall comprising a valve seat, said transverse wall having an exhalation opening therethrough and an adjacent anchor opening through said transverse wall, said exhalation valve including a valve closure element comprising a head and an integral stem of plastic material, said head normally covering said exhalation opening and disposed relatively toward the exterior of said mask and said stem extending into said anchor opening to anchor said head, said head resiliently moving at least in part from said exhalation opening upon exhalation.

10. A mask as set forth in claim 9 wherein said stem extends entirely through said transverse wall and has an enlargement thereon engaging said transverse wall opposite to said valve member head.

11. A mask for the exhalation of medication by a human being, said mask being molded of plastic material or the like having an interior and a through opening comprising an open front portion receiving a hollow body having air with medication dispersed therein, said mask comprising means for minimizing dead space inside said mask yet providing efficient inhalation and exhalation flow paths that purge said mask of exhaled air;

a one-way inhalation valve for said mask, said inhalation valve normally being closed and opening upon inhalation, a sidewall expanding outwardly from said front portion to a rear portion adapted to fit sealingly on a human face and covering the mouth and nose, said sidewall including a forward extension projecting outwardly of said sidewall and substantially parallel thereto, and adapted to overlie a nose, said extension extending substantially from said rear portion toward said front portion, and means for providing a short exhalation flow path comprising a normally closed one-way exhalation valve adjacent said extension adapted for positioning directly adjacent the nostrils of the nose, said exhalation valve opening on exhalation to pass exhaled air from said mask and closing in the absence of exhaled air to prevent entry of outside air, said inhalation valve and said exhalation valve holding air with medication in said mask for most effective utilization of said medication.

12. A mask for the inhalation of medication by a human being, said mask being molded of a plastic material or the like having an interior and a central through opening including an open front portion for receiving a hollow body having aerosol with medication dispersed therein, a substantially frusto-conical sidewall expanding outwardly from said front portion to a rear portion adapted to fit sealingly on a human face and covering the mouth and nose, said mask comprising means for minimizing dead space inside said mask yet providing efficient inhalation and exhalation flow paths that purge said mask of exhaled air including a tunnel-like extension projecting outwardly of said mask sidewall and substantially parallel thereto, and adapted to overlie a human nose, said extension extending substantially from said rear portion toward said front portion and having a front end terminating short of said front portion of said mask, and means for providing a short exhalation flow path comprising a normally closed one-way exhalation valve adjacent said front end of said extension adapted for positioning directly adjacent the nostrils of the nose, said exhalation valve communicating on one side inwardly of said mask into said extension and on the other side communicating outwardly of said mask to outside air, said exhalation valve having a quick acting lightweight valve body extending outwardly from a central stem to provide a light weight seal on the outside edge of said exhalation valve, said valve body providing a minimum resistance to exhaled air and quick response to exhalation of air and minimizing the amount of exhaled air retained in said mask, said exhalation valve closing in the absence of exhaled air to prevent entry of outside air.

13. A mask as set forth in claim 12 wherein said valve is positioned in its entirety short of said mask extension to reduce access to prying fingers.

14. A mask as set forth in claim 13 and further including a transverse wall adjacent the end of said nose receiving extension relatively toward the mask open front portion, an exhalation opening through said transverse wall, said valve including a valve closure member.

15. In combination:

a source for providing an aerosol of medication upon activation;

an aerosolization chamber for receiving the aerosol from said source of aerosol medication, said aerosolization chamber having an exit end with a first valve to prevent flow into said aerosolization chamber from said exit end; and a mask having an inlet connected to the exit end of the aerosolization chamber, said inlet in alignment with a mouth of a patient wearing said mask, wherein said mask has minimal dead space inside yet provides efficient inhalation and exhalation flow paths that purge said mask of exhaled air;

and further wherein said mask provides a short exhalation flow path comprised of a second valve located in an opening adjacent said inlet and into said mask, said second valve adapted for positioning directly adjacent the nostrils of the nose, said second valve adapted to permit air flow through said opening upon exhalation into said mask so as to permit a patient wearing said mask to exhale air through said opening, and to prevent air flow through said opening upon patient inhalation;

and further wherein said first valve in said exit end of said aerosolization chamber permits flow from said aerosolization chamber into said mask, but not vice versa.

16. The invention of claim 15 in which said second valve is adapted to open when the pressure across the valve is 0.50 inch of water above ambient.

17. The invention of claim 15 in which said mask has a diameter of approximately 3 inches.

18. The invention of claim 15 in which said mask has a length of approximately just over two inches.

19. The invention of claim 15 in which the second valve is inaccessible manually.

20. The invention of claim 15 in which said closed mask is sized to cover a patient's nose and mouth.

21. The invention of claim 15 in which said mask is sized to cover a nose and mouth of an infant.

22. The invention of claim 15 in which said mask is sized to cover a nose and mouth of an elderly person.

23. The invention of claim 15 in which an upper edge of said mask is sized to fit against a patient's face between the patient's eyes and nose.

24. The invention of claim 15 wherein said source for providing an aerosol of medication is a metered dose inhaler.

25. An improved system for delivering aerosol medication to an infant, the system using a metered dose inhaler for producing an aerosol of medication upon activation and an aerosolization chamber for receiving the aerosol produced from said metered dose inhaler, the aerosolization chamber having an exit end with a first valve to prevent flow into said aerosolization chamber from said exit end, the improvement comprising:

a close-fitting mask comprising:

an inlet connected to the exit end of the aerosolization chamber so that said inlet is aligned with a mouth of an infant wearing said mask to provide minimal dead space inside said mask yet provide efficient inhalation and exhalation flow paths that purge said mask of exhaled air; and wherein said mask comprises a short exhalation flow path comprised of a second valve covering an opening through said close-fitting mask, said second valve having a low threshold of operation so as to permit air flow through said opening from said mask upon exhalation, said second valve adapted for positioning directly adjacent the nostrils of the nose, and further wherein said first valve in said exit end of said aerosolization chamber permits flow from said aerosolization chamber into said mask, but not vice versa.

26. A method of delivering a medication to an infant comprising:

providing a metered dose inhaler having an output thereof connected to a chamber, said chamber having an exit end with a first valve therein to prevent air flow into said chamber from said exit end, and a mask having an inlet connected to the exit end of the aerosolization chamber, said mask comprising a short exhalation flow path comprised of a second valve adapted to open upon exhalation into said mask, said second valve adapted for positioning directly adjacent the nostrils of the nose, and further wherein said mask comprises minimal dead space inside said yet provides efficient inhalation and exhalation flow paths that purge said mask of exhaled air;

positioning the mask over a mouth and nose of the infant so that said inlet of said mask is aligned with the mouth of the infant;

actuating the metered dose inhaler to provide an aerosol of medication into the chamber; and maintaining the mask on the infant while observing at least one exhalation of the infant through the second valve.

27. The method of claim 26 further comprising the step of maintaining the mask on the infant for a first and second inhalation.

* * * * *

UNITED STATES PATENT AND TRADEMARK OFFICE
CERTIFICATE OF CORRECTION

PATENT NO. : 5,645,049
DATED : July 8, 1997
INVENTOR(S) : Martin P. Foley et al.   Page 1 of 2

It is certified that error appears in the above-identified patent and that said Letters Patent is hereby corrected as shown below:

On the Title Page

In column 1, item [75], after "London," please insert --Ontario,--.

In column 1, item [73], after "London," please insert --Ontario,--.

In the Claims

In claim 1, line 9, please change ";" (semicolon) to --,-- (comma).

In claim 9, line 8, after "air", please insert --,-- (comma).

In claim 11, line 5, after "comprising", please insert --:-- (colon).

In claim 11, line 8, please change ";" (semicolon) to --,-- (comma).

UNITED STATES PATENT AND TRADEMARK OFFICE
CERTIFICATE OF CORRECTION

PATENT NO. : 5,645,049
DATED : July 8, 1997
INVENTOR(S) : Martin P. Foley et al.   Page 2 of 2

It is certified that error appears in the above-identified patent and that said Letters Patent is hereby corrected as shown below:

<u>In the Claims (cont'd)</u>

In claim 12, line 3, after "having", please insert --:-- (colon).

In claim 26, line 13, after "said", please insert --mask--.

Signed and Sealed this

Twenty-seventh Day of March, 2001

*Attest:*

NICHOLAS P. GODICI

*Attesting Officer*   *Acting Director of the United States Patent and Trademark Office*